United States Patent [19]

Volles et al.

[11] Patent Number: 4,608,061

[45] Date of Patent: Aug. 26, 1986

[54] NORMAL BUTANE/ISO-BUTANE SEPARATION

[75] Inventors: Warren K. Volles, Mt. Kisco; Nelson A. Cusher, Carmel, both of N.Y.

[73] Assignee: Union Carbide Corporation, Danbury, Conn.

[21] Appl. No.: 749,784

[22] Filed: Jun. 28, 1985

[51] Int. Cl.[4] .............................................. B01D 53/04
[52] U.S. Cl. .................................... 55/26; 55/62; 55/68; 208/310 Z; 585/820
[58] Field of Search ................... 55/25, 26, 62, 68, 75; 208/310 Z; 585/820, 822, 826

[56] References Cited

U.S. PATENT DOCUMENTS

| | | | |
|---|---|---|---|
| 3,176,444 | 5/1965 | Kiyonaga | 55/26 |
| 3,226,913 | 1/1966 | Avery | 55/25 |
| 3,226,914 | 1/1966 | Griesmer et al. | 55/62 X |
| 3,422,003 | 1/1969 | Anstey et al. | 208/310 Z |
| 3,422,005 | 1/1969 | Avery | 208/310 |
| 3,430,418 | 3/1969 | Wagner | 55/25 |
| 3,700,589 | 10/1972 | Symoniak et al. | 208/310 |
| 3,986,849 | 10/1976 | Fuderer et al. | 55/25 |
| 4,059,505 | 11/1977 | Cartwright et al. | 208/310 Z |
| 4,176,053 | 11/1979 | Holcombe | 208/310 Z |
| 4,350,583 | 9/1982 | Fuderer | 208/310 Z |
| 4,374,022 | 2/1983 | Fuderer | 208/310 Z |
| 4,406,674 | 9/1983 | Knoblauch et al. | 55/62 X |
| 4,476,345 | 10/1984 | Gray, Jr. et al. | 208/310 Z X |

*Primary Examiner*—Robert Spitzer
*Attorney, Agent, or Firm*—Aziz M. Ahsan; A. H. Fritschler

[57] ABSTRACT

Iso-butane is separated from normal butane in a pressure swing adsorption system of at least three adsorbent beds, each adapted to selectively adsorb normal butane from a mixture thereof with iso-butane. The adsorption front of normal butane formed in each adsorbent bed upon the passage of the feed gas mixture thereto is moved through the bed to an extent enhancing the utilization of the adsorptive capacity thereof. By combinations of depressurization and repressurization together with purge, desirable product purity levels are obtained, while the costs of adsorbent equipment and of operation are reduced to the extent possible consistent with the purity requirements of a given application.

21 Claims, No Drawings

NORMAL BUTANE/ISO-BUTANE SEPARATION

BACKGROUND OF THE INVENTION

1. Field of the Invention

The invention relates to the separation of iso-butane and normal butane. More particularly, it relates to an improved adsorption process for achieving such separation.

2. Description of the Prior Art

Various techniques are known in the art for the separation of normal hydrocarbons from non-normal hydrocarbons. One such separation of practical commercial significance is the separation of iso-butane from normal butane, with said n-butane being used for gasoline vapor pressure blending purposes, and the iso-butane being used for the production of high octane alkylates for gasoline. Other uses of isobutane include the production of tertiary butyl alcohol (TBA), an octane enhancer, and other useful petrochemicals. Iso-butane and normal butane are commonly separated by distillation techniques that are effective but, nevertheless, are highly energy intensive. Adsorption techniques are also known for the separation of branched chain hydrocarbons from straight chain hydrocarbons and can be employed for the separation of iso-butane from normal butane. It will be appreciated that, unlike distillation, adsorption does not require any reflux to produce high purity products. Iso-butane separation from normal butane was the subject of Example 4 of the Kiyonaga patent that disclosed a basic processing feature upon which desirable pressure swing adsorption (PSA) operations in multi-bed adsorption systems have been developed. In the PSA process, a feed gas mixture to be separated is introduced at an upper adsorption pressure to the feed end of an adsorption bed capable of selectively adsorbing a more readily adsorbable component from a less readily adsorbable component of the feed gas mixture that passes through the bed and is removed from the discharge end thereof. The bed is thereafter depressurized to a lower adsorption pressure for removal of the more readily adsorbable component therefrom. In the early development of the PSA process, the adsorption step was carried out until the adsorption front of more readily adsorbable component formed in the bed reached the discharge end of the bed so as to take advantage of the full adsorptive capacity of the bed. Kiyonaga, on the other hand, disclosed the termination of the adsorption step before the adsorption front reaches said discharge end of the bed and before the more readily adsorbable component breaks through into the stream of less readily adsorbable component gas. The adsorption step is followed by a cocurrent depressurization step in which the bed is partially depressurized by the discharge of void space gas, essentially less readily adsorbable component, from the discharge end of the bed. As is disclosed by the Wagner patent, U.S. Pat. No. 3,430,418 and the Fuderer et al, patent, U.S. Pat. No. 3,486,849, the void space gas released during one or more cocurrent depressurization steps is commonly used for pressure equalization purposes between beds and to provide purge gas to a bed in the system at its lower desorption pressure.

In the two bed separation of iso/normal butane as recited by Kiyonaga, a lower desorption pressure in the vacuum range was employed, and a quantity of the less readily adsorbable component was used to countercurrently repressurize the evacuated bed to the upper adsorption pressure. While the PSA process of Kiyonaga, and the cocurrent depressurization feature thereof, constitute a significant advance in the development of the PSA art, there remains a desire in the art for the development of further improvements, as with respect to the separation of iso-butane and normal butane. With respect to this separation, it is desired to employ a process that is less costly to operate than that of Kiyonaga and that employs a less costly adsorption system for the carrying out of the process than is possible in accordance with the teachings of Kiyonaga.

It is an object of the invention, therefore, to provide an improved process for the separation of iso-butane and normal butane.

It is another object of the invention to provide a PSA process capable of enhanced operation in separating said iso-butane and normal butane.

With these and other objects in mind, the invention is hereinafter described in detail, the novel features thereof being particularly pointed out in the appended claims.

SUMMARY OF THE INVENTION

Both normal butane and iso-butane are recovered with enhanced purity in the process of the invention, with enhanced bed utilization and productivity being achievable by a particular sequence of countercurrent depressurization and purge steps. In variations of the basic processing sequence, other depressurization steps can be employed to particularly enhance the purity of one or both products while utilizing the adsorptive capacity of the bed to the extent possible consistent with the purity requirements of a particular embodiment.

DETAILED DESCRIPTION OF THE INVENTION

The objects of the invention are achieved, in the first instance, by a basic processing sequence described and claimed herein. This sequence enables enhanced bed utilization and productivity to be achieved at advantageous adsorbent and capital equipment requirements, and advantageous operating expenses, while the desired separation of normal butane and iso-butane is expeditiously achieved at desirable purity levels of the recovered products.

While molecular sieve adsorption has been used commercially for various iso/normal paraffin separations in the naphtha and kerosene boiling ranges, adsorption has not been so used commercially for butane separation because of its lack of economic competitiveness with distillation. Thus, distillation is generally used to separate iso-butane and normal butane in routinely practiced operations in petroleum refining and natural gas liquids (NGL) processing plants. The basic processing sequence provides a highly desirable economic alternative for accomplishing the subject butane separation. Th alternate embodiment of the invention also described and claimed enables the convenient separation of butanes by adsorption to be adjusted to the particular purity requirements of a given application.

In the basic processing sequence, a feed gas mixture of iso-butane and normal butane at an upper adsorption pressure is introduced to the feed end of a bed capable of selectively adsorbing normal butane as the more selectively adsorbable component of said gas mixture. Iso-butane is thus the less readily adsorbable component, and it passes through the bed and is discharged from the discharge end thereof. It will be understood that said bed is a part of an adsorption system having at least three such beds, each of which has the feed gas mixture passed thereto and which otherwise undergoes, on a cyclic basis, the overall processing sequence as described herein. The feed gas mixture is passed to each bed, in turn, with the feed as introduction being continued as a normal butane adsorption front is formed in the bed and passes through the bed from the feed end of the bed in the direction of the discharge end thereof. In the practice of said basic processing sequence, the normal butane adsorption front is allowed to break through at the discharge end of the bed. As is described below, a portion of the iso-butane effluent stream thus discharged is not recovered as product, but is diverted for passage as purge gas to another adsorbent bed in the system.

Upon completion of said adsorption step which will be seen to depart from the teachings of the Kiyonaga patent, the bed is countercurrently depressurized with release of gas from the inlet end thereof, thereby depressurizing said bed to an intermediate pressure. The released gas is passed to another bed in the system initially at a lower pressure for pressure equalization with said bed at the intermediate pressure. The bed is then further countercurrently depressurized with release of an additional amount of gas from the inlet end thereof, thereby depressurizing said bed to a lower desorption pressure. The gas released during this step is recovered as normal butane product gas.

Following said recovery of normal butane product, the bed is countercurrently purged by the addition of iso-butane purge gas to the discharge end thereof. It will be appreciated that said purge gas comprises the portion of iso-butane effluent gas obtained during the adsorption step in a bed in the system that is diverted for use as said purge gas, the diverted portion of said gas conveniently, but not necessarily, being that obtained at the end of the adsorption step. The introduction of the purge gas is continued just long enough to sweep void space gas from the bed, but without breakthrough of iso-butane into the normal butane product. Thus, residual normal butane present in the void space of the bed is purged to enhance the recovery of normal butane product gas and the purity thereof.

Following said purge, the bed is partially repressurized by the passage of countercurrent depressurization effluent from a different bed in the system initially at a higher pressure for pressure equalization between said beds at said intermediate pressure level as referred to above. In this regard, it should be noted that the process is described herein essentially as pertains to a three bed system in which there would be one such intermediate pressure. In other embodiments having a larger number of beds in the system, it will be appreciated that more than one such intermediate pressure would likely be employed so as to accommodate the processing sequence to the number of beds employed. In the final steps of the sequence, the bed is further repressurized from the intermediate pressure level to said upper adsorption pressure by the addition of feed gas to said bed. The repressurization of the bed from lower desorption pressure to upper adsorption pressure, as by said pressure equalization step and said final repressurization, are both preferably and advantageously carried out by the addition of gas to the feed end of the bed.

In the practice of the invention, the initial adsorption step in which the adsorption front is allowed to break through at the discharge end of the bed is carried out until the stoichiometric point of the adsorption front reaches from about 90% to about 100% of the length of the bed from the feed end thereof. As employed herein and is commonly understood in the art, the stoichiometric point of the front will be understood to constitute the mid-point between the leading, forward edge of said front with the trailing, backward edge thereof. In the normal butane/iso-butane separation of present interest, the breakthrough of the adsorption front at the discharge end of the bed, i.e., the reaching of the leading edge of said front at the 100% point of the length of the bed, occurs when the stoichiometric point is approximately 80 to 90% through the bed length. As the stoichiometric point advances to said about 90–100% of bed length, a greater amount of the adsorption front will have passed out of the bed and the trailing edge of the front will have moved closer to the discharge end of the bed, as to approximately 90% of the bed length. In preferred embodiments, it is the iso-butane effluent stream discharged upon reaching of breakthrough conditions that is diverted for use as purge gas for another bed in the system.

The purge step using said purge gas obtained from iso-butane effluent gas is desirably continued until up to about 80% to about 100% of the void space gas between the adsorbent particles is displaced in the direction of the feed end of the bed and is discharged from the feed end thereof.

It will be appreciated that various changes and modifications can be made in the process hereinabove described with reference to a basic processing sequence of (1) adsorption at upper adsorption pressure, (2) countercurrent depressurization-pressure equalization, (3) countercurrent depressurization to lower desorption pressure, (4) countercurrent purge with adsorption effluent gas, (5) partial repressurization-pressure equalization, and (6) final repressurization, as with feed gas, to upper adsorption pressure, without departing from the scope of the invention as set forth in the claims. Thus, the upper adsorptive pressure is preferably maintained at from about 100 psia to about 300 psia, but pressures outside such limits can also be employed. At pressures below about 100 psia, however, the change in loading, sometimes referred to as the delta loading, between the adsorption and the desorption pressures becomes small, making the process less efficient than is generally desired. At pressures above about 300 psia, on the other hand, the increases in the delta loading become small as the amount of feed stored in the voids increases proportionally with the increase in pressure.

The adsorption system employed in the practice of the invention will comprise at least three beds with a three-bed system being convenient although larger systems, having from four to six adsorbent beds or more, can also be employed. Operating temperatures are typically in the range of from about 400° F. to about 600° F. In general, operating at below about 400° F. will yield a low desorption, i.e., normal butane, product purity because of the relatively large amount of feed gas stored in the void spaces of the adsorbent. At temperatures greater than 600° F., however, only small improvements in performance are found to occur such as not to justify the increased heat requirements for such high temperature operation.

Depending upon the source of the feedstock employed, the composition thereof will generally vary in normal butane concentration from about 30% to about 70% by volume based on the overall volume of feed gas mixture employed. Butane feedstocks outside this range of composition can also be encountered, however, and can be treated in accordance with the invention. Feedstocks that are relatively high in normal butane content yield relatively high delta loadings and thus higher desorption product purities. It should also be noted that the total cycle time for each cycle of the processing sequence of the invention can vary widely, although a total cycle time of from about three minutes to about six muntes is commonly desirable. Relatively short cycles are most advantageous because of the lesser adsorbent requirements thereof as compared with longer cycle times. At cycle times below about three minutes, however, bed lifting and adsorbent particle crushing problems can become severe. However, cycle times of on the order of twenty minutes or more may be appropriately used in some circumstances, as in the conversion of existing adsorption equipment for butane separations.

It will be understood that the resultant purities of normal butane and iso-butane obtained are variable and are dependent upon the various processing features and operating parameters referred to above. The countercurrent depressurization—pressure equalization step has been found to enhance normal butane desorption product gas purity, while the countercurrent purge step may result in a significant improvement in purity and recovery of both products.

At the end of the adsorption step, essentially feed composition gas is found in the non-selective voids of the adsorbent bed as a result of the packing of the adsorbent material in the bed. The countercurrent depressurization-pressure equalization step alters this void space gas to be removed, ultimately improving the final desorption normal butane product purity as well as the recovery of iso-butane. In experimental comparisons, the desorption normal butane product purity was improved by 9 wt. %, i.e. from 70% to 79% by the addition of said countercurrent depressurization step to 110 psia, with an upper adsorption pressure of 200 psia, lower desorption pressure of 20 psia, countercurrent purge at said 20 psia, and temperature of 400° F., using a 50% normal butane feed and with a constant iso-butane product purity of 90 wt %. In similar comparisons, the countercurrent purge step resulted in a 12 wt % of improvement in iso-butane purity, i.e., from 83% to 95%, likewise with an upper adsorption pressure of 200 psia, countercurrent desorption to 20 psia, said purge being carried out at 20 psia, and a temperature of 400° F., using said 50% normal butane—50% iso-butane feed, and with a constant normal butane product purity of 68%. The front sharpening effect resulting from the purge step also allows more feed gas to be processed per weight of adsorbent resulting in a savings in the amount of adsorbent required.

Whereas the prior art adsorption approach utilizes about 50% of the adsorptive capacity of the bed during the adsorption step, with the remainder utilized during cocurrent depressurization, the subject invention, incorporating a countercurrent depressurization—pressure equalization step, allows more complete utilization of said adsorptive capacity, (e.g. up to about 90%), and thus further requires less adsorbent to perform a given separation operation. This results not only in higher productivity and lower adsorbent costs, but also in lower capital equipment costs due to the smaller adsorber vessels required. In addition, the countercurrent depressurization—pressure equalization step is further advantageous in that it eliminates the need for a low range vacuum desorption step, as to about 1 psia, as is used in the prior art adsorption technique. The operating costs associated with the practice of the invention are thereby also favorably reduced as compared to prior art processing technique.

The advantages of the invention will be further seen from the following example presented for illustrative purposes only and not to be taken as limiting the scope of the invention as set forth in the appended claims. A three-bed adsorption system is designed to treat 8,000 barrels per standard day (66,960 lb/hr) of a 50% iso-butane/50 mole % normal butane feedstock at 400° F. using 38,900 lbs of 1/8 inch Linde Type 5A molecular sieve adsorbent pellets in each of the three adsorbent beds. In carrying out the process using the basic processing sequence as described above, 30,213 lb/hr of liquid isobutane product can be removed upon condensation at 130° F., 100 psia, with the product composition being 95 mole % iso-butane and 5% normal butane. The normal butane product recoverable in liquid state at 40° F., 100 psia in the amount of 36,747 lb/hr has a composition of 87 mole % normal butane and 13 mole % of iso-butane. Total cycle time is 3.75 minutes, with said cycle being isothermal at 500° F., with the upper adsorption pressure being 200 psia and the adsorption step being terminated when the stoichiometric point of the adsorption front reaches about 95% utilization. The pressure equalization step is carried out to an intermediate pressure of about 110 psia, with subsequent countercurrent desorption to, and purge at, 20 psia. The countercurrent purge using diverted iso-butane adsorption effluent gas flushes out most of the normal butane that otherwise would tend to remain in the macropores and void spaces of the bed as the bed approaches lower desorption pressure, but is terminated before a large quantity of iso-butane breaks through into the desorption effluent.

Those skilled in the art will readily appreciate that various other changes and modifications can be made in the details of the invention within the scope of the appended claims. For example, the adsorbent employed can be any suitable, conveniently available adsorbent capable of selectively adsorbing said normal butane as a more readily adsorbable component of the feed gas mixture, while iso-butane as the less readily adsorbable component is preferentially passed through a bed of said adsorbent and discharged from the discharge end of said bed. Synthetic molecular sieves, such as standard 5A ⅛" pellets marketed by Union Carbide, are suitable for use in the practice of the invention. The subject normal butane/iso-butane adsorption separation can be described as size selective, in that said molecular sieve crystals have interconnecting pores of a precisely uniform size to accept molecules with a minimum effective diameter of up to five angstroms. As a result, normal paraffins can pass through the pores with the main adsorption sites, while larger diameter non-normal hydrocarbons are excluded from said pores and thus pass through the bed of molecular sieve material. High density 5A ⅛" pellets are a preferred adsorbent for purposes of the invention because they have a higher packed bed density, i.e., about 53 lb/ft$^3$, and thereby less void space, than in the standard 5A ⅛" pellets having a density of about 43 lb/ft$^3$. It should be appreciated that the adsorbents useful for the normal butane/iso-butane separation of particular interest are also capable, as indicated above, of separating other normal hydrocarbon/non-normal hydrocarbon mixtures, and that the basic processing sequence, and variations thereof, as herein described and claimed, can also be employed for such other separations. Thus, the separation of n-pentane and iso-pentane in adsorption systems having three or more beds is a useful application for the extension of the subject invention to the treatment of mixtures other than normal butane and iso-butane.

The invention provides a practical and convenient alternative to the use of distillation for the separation of iso-butane from normal butane in petroleum refining, natural gas liquids processing plants and the like. The enhanced bed utilization and adsorbent productivity achieved, combined with variations adapted to minimize energy requirements and costs and/or to enable enhanced product purities to be achieved, provide a desirable advance in the PSA field and provides a highly desirable extension of the PSA technology in meeting the gas separation requirements encountered in practical commercial activities.

We claim:

1. An improved pressure swing adsorption process for the separation of iso-butane from normal butane in an adsorption system having at least three adsorbent beds, each bed of which undergoes, on a cyclic basis, a processing sequence comprising:
    (a) introducing a feed gas mixture of iso-butane and normal butane at an upper adsorption pressure to the feed end of the bed capable of selectively adsorbing normal butane as the more selectivity adsorbable component of the gas mixture, while iso-butane as the less readily adsorbable component passes through the bed and is discharged from the discharge end thereof, such feed gas introduction being continued as a normal butane adsorption front is formed in the bed and passes through the bed from the feed end thereof and breaks through at the discharge end of the bed, a portion of the iso-butane effluent stream thus discharged being diverted for passage as purge gas to another bed in the system;
    (b) countercurrently depressurizing said bed with release of gas from the feed end thereof, thereby depressurizing said bed to an intermediate pressure, said released gas being passed to another bed initially at a lower pressure for pressure equalization at said intermediate pressure;
    (c) further countercurrently depressurizing said bed with release of additional amounts of gas from the feed end thereof, thereby depressurizing said bed to a lower desorption pressure, the gas released being recovered as normal butane product gas;
    (d) countercurrently purging said bed by the addition of iso-butane purge gas to the discharge end thereof, thereby purging residual normal butane present in the void spaces of the bed to enhance the recovery of normal butane product gas and the purity thereof;
    e) partially repressurizing said bed by the passage of countercurrent depressurization effluent gas from a bed in the system initially at a higher pressure for pressure equalization therebetween at said intermediate pressure level; and
    (f) further repressurizing said bed from the intermediate pressure to said upper adsorption pressure by the addition of feed gas thereto,
    whereby enhanced bed utilization and productivity are achieved at advantageous adsorbent and captial equipment requirements, and advantageous operating expenses, for the desired gas separation operation.

2. The process of claim 1 in which the repressurization of the bed in steps (e) and (f) is carried out cocurrently by the addition of gas to the feed end of the bed.

3. The process of claim 2 in which said introduction of the feed gas mixture to the bed in step (a) is carried out until the stoichiometric point of the adsorption front reaches from about 90% to about 100% of the length of the bed.

4. The process of claim 3 in which said countercurrent purge step (d) is continued until up to about 80% to about 100% of the void space gas between the adsorbent particles in the bed is displaced in the direction of the feed end of the bed and is discharged from the feed end thereof.

5. The process of claim 4 in which the iso-butane purge gas comprises the portion of the iso-butane effluent stream diverted from a bed for use as purge gas in step (a) as carried out in that bed.

6. The process of claim 5 in which said upper adsorption pressure is from about 100 to about 300 psia.

7. The process of claim 6 in which said lower desorption pressure is in the range of from about 5 to about 20 psia.

8. The process of claim 6 in which said adsorption system comprises three adsorbent beds.

9. The process of claim 8 in which said lower desorption pressure is in the range of from about 5 to about 20 psia.

10. The process of claim 9 in which the reaction temperature is from about 400° F. to about 600° F.

11. The process of claim 10 in which the feed gas mixture has a normal butane concentration of from about 30% to about 70% by volume.

12. The process of claim 6 in which said adsorption system comprises from four to six adsorbent beds.

13. The process of claim 12 in which said lower desorption pressure is in the range of from about 5 to about 20 psia.

14. The process of claim 12 in which said adsorption system comprises four beds.

15. The process of claim 12 in which the reaction temperature is from about 400° F. to about 600° F.

16. The process of claim 15 in which the feed gas mixture has a normal butane concentration of from about 30% to about 70% by volume.

17. The process of claim 3 in which said upper adsorption pressure is from about 100 to about 300 psia.

18. The process of claim 17 in which said lower desorption pressure is in the range of from about 5 to about 20 psia.

19. The process of claim 1 in which the reaction temperature is from about 400° F. to about 600° F.

20. The process of claim 1 in which the feed gas mixture has a normal butane concentration of from about 30% to about 70% by volume.

21. The process of claim 1 in which the overall time for each processing cycle is from about 3 to about 6 minutes.

* * * * *

UNITED STATES PATENT AND TRADEMARK OFFICE
CERTIFICATE OF CORRECTION

PATENT NO. : 4,608,061

DATED : August 26, 1986

INVENTOR(S) : Warren K. Volles and Nelson A. Cusher

It is certified that error appears in the above-identified patent and that said Letters Patent is hereby corrected as shown below:

At the eleventh line of the Abstract, "costs of adsorbent equipment" should read --cost of adsorbent, equipment--.

Column 3, line 7, "as" should read --gas--.

Signed and Sealed this

Twenty-ninth Day of September, 1987

Attest:

DONALD J. QUIGG

*Attesting Officer*   *Commissioner of Patents and Trademarks*